(12) United States Patent
Lai (10) Patent No.: US 11,363,988 B2
(45) Date of Patent: Jun. 21, 2022

(54) SYSTEMS AND METHODS FOR ACCELERATED MRI SCAN

(71) Applicant: GENERAL ELECTRIC COMPANY, Schenectady, NY (US)

(72) Inventor: Peng Lai, Menlo Park, CA (US)

(73) Assignee: General Electric Company, Schenectady, NY (US)

( * ) Notice: Subject to any disclaimer, the term of this patent is extended or adjusted under 35 U.S.C. 154(b) by 969 days.

(21) Appl. No.: 16/112,965

(22) Filed: Aug. 27, 2018

(65) Prior Publication Data

US 2018/0360384 A1    Dec. 20, 2018

Related U.S. Application Data

(63) Continuation of application No. 14/244,856, filed on Apr. 3, 2014, now abandoned.

(60) Provisional application No. 61/808,574, filed on Apr. 4, 2013.

(51) Int. Cl.
| | | |
|---|---|---|
| A61B 5/055 | (2006.01) | |
| G01R 33/54 | (2006.01) | |
| A61B 5/00 | (2006.01) | |
| G01R 33/563 | (2006.01) | |
| G01R 33/561 | (2006.01) | |
| G01R 33/565 | (2006.01) | |

(52) U.S. Cl.
CPC ............ *A61B 5/7214* (2013.01); *A61B 5/055* (2013.01); *G01R 33/56325* (2013.01); *A61B 5/0044* (2013.01); *A61B 5/742* (2013.01); *A61B 5/7475* (2013.01); *A61B 2576/023* (2013.01); *G01R 33/5611* (2013.01); *G01R 33/56545* (2013.01)

(58) Field of Classification Search
CPC ..... A61B 5/7214; A61B 5/055; A61B 5/0044; A61B 5/742; A61B 5/7475; G01R 33/5611; G01R 33/055; G01R 33/56545
See application file for complete search history.

(56) References Cited

U.S. PATENT DOCUMENTS

| | | | | |
|---|---|---|---|---|
| 2005/0100202 A1* | 5/2005 | Huang | ............... | G01R 33/5611 382/128 |
| 2005/0271297 A1* | 12/2005 | Zbilut | ...................... | G06K 9/62 382/286 |
| 2008/0278160 A1* | 11/2008 | Griswold | ........... | G01R 33/5611 324/307 |
| 2009/0092303 A1* | 4/2009 | Griswold | ........... | G01R 33/5611 382/131 |
| 2014/0035576 A1* | 2/2014 | Li | ...................... | G01R 33/5611 324/309 |

* cited by examiner

*Primary Examiner* — Patricia J Park (57) ABSTRACT

A method of processing signals from an accelerated MRI scan of a dynamic event occurring in the body of a human patient. The patient is subjected to an MRI examination which includes the relevant portion of his body. Those voxels for which there is no substantially no change over the time of the scan are identified and subtracted from the overall scan signal.

12 Claims, 5 Drawing Sheets

SYSTEMS AND METHODS FOR ACCELERATED MRI SCAN

CROSS-REFERENCE

This application is a continuation application of U.S. patent application Ser. No. 14/244,856 filed on Apr. 3, 2014, which claims benefit and priority to U.S. Provisional Application No. 61/808,574 filed on Apr. 4, 2013. Both are incorporated herein by reference in entirety.

BACKGROUND

The MRI imaging of tissues in the human body involves the generation of substantial amounts of signal data which must be appropriately processed to generate video images understandable to medical personnel. The amount of signal data needed to render a good quality image increases significantly when some of the tissue being imaged is moving as it is being imaged, for instance when a beating heart is in the chest is being imaged. In such case the signal data includes signals generated by the moving tissue and the static tissue which is adjacent to the moving tissue. The amount of signal data needed from the moving tissue is substantially greater than that needed from the static tissue because of the need to properly account for the motion. The situation is analogous to the need for a higher shutter speed on a camera when photographing a moving object. However, the time for both signal acquisition and signal processing in the MRI imaging of human patients is limited by practical considerations. For instance, in cardiac imaging it is common to have the patient hold his breath limiting the time for the acquisition of a given data set to about twenty seconds. Furthermore, it is desirable for medical personnel to be able to examine the images before releasing the patient so the time for data processing is also limited. Techniques in data processing, including reconstruction in K-space, have been developed to reduce the amount of signal data needed and thus allow accelerated MRI, but the results in terms of both image quality and processing time are less than optimum.

SUMMARY

A method of processing signals from a magnetic resonance imaging scan of a dynamic event occurring in the body of a patient includes accessing original magnetic resonance imaging data of a relevant portion of a patient's body. A subset of time spaced frames are created from the original magnetic resonance imaging data. Static tissue voxels representing static tissue are identified by comparing a change in each voxel signal between the subset of time spaced frames. The signals of the static tissue voxels are removed from the original magnetic resonance imaging data to create a modified magnetic resonance imaging data. The modified magnetic resonance imaging data is reconstructed.

In one embodiment a method of processing signals from an accelerated MRI scan of a dynamic event occurring in the body of a human patient. The patient is subjected to an MRI examination which includes the relevant portion of his body. Those voxels for which there is no substantially no change over the time of the scan are identified and subtracted from the overall scan signal.

In another embodiment a method of processing signals from an accelerated MRI scan of a dynamic event occurring in the body of a human patient includes obtaining an MRI examination which includes the relevant portion of a patient. The method further includes identifying those voxels for which there is substantially no change over the time course of the scan. The method also includes subtracting signals of those voxels from the original scan signal to improve image reconstruction in accelerated MRI.

In another embodiment a data processor for processing signals from an accelerated MRI scan of a dynamic event occurring in the body of a human patient who has had the relevant portion of his body subject to an MRI examination. The data processor has elements which acquire the scan signals from several different time windows such that the voxels in which there is motion associated with the dynamic event will each provide a recognizably different signal for each time window, identify those voxels for which there is a significant signal which has substantially no change between the sampled time windows, and subtract those voxels from the overall scan signal.

DETAILED DESCRIPTION

Figure 1:
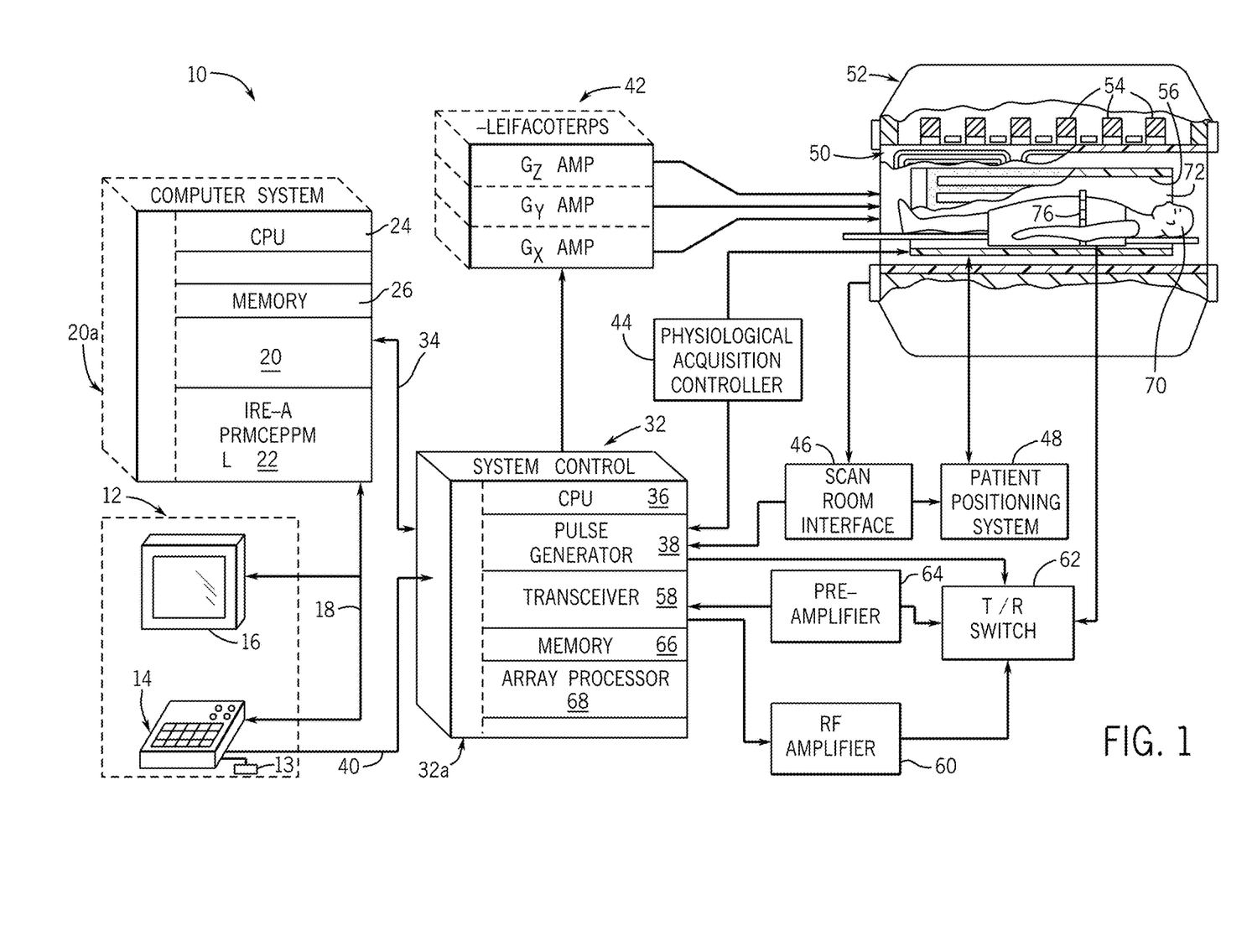
FIG. 1 is a schematic block diagram of an exemplary magnetic resonance imaging (MRI) system in accordance with an embodiment.

Referring to FIG. 1, FIG. 1 is a schematic block diagram of an exemplary magnetic resonance imaging (MRI) system in accordance with an embodiment. The operation of MRI system 10 is controlled from an operator console 12 that includes a keyboard or other input device 13, a control panel 14, and a display 16. The console 12 communicates through a link 18 with a computer system 20 and provides an interface for an operator to prescribe MRI scans, display resultant images, perform image processing on the images, and archive data and images. The computer system 20 includes a number of modules that communicate with each other through electrical and/or data connections, for example, such as are provided by using a backplane 20a. Data connections may be direct wired links or may be fiber optic connections or wireless communication links or the like. The modules of the computer system 20 include an image processor module 22, a CPU module 24 and a memory module 26 which may include a frame buffer for storing image data arrays. In an alternative embodiment, the image processor module 22 may be replaced by image processing functionality on the CPU module 24. The computer system 20 is linked to archival media devices, permanent or back-up memory storage or network. Computer system 20 may also communicate with a separate system control computer 32 through a link 34. The input device 13 can include a mouse, joystick, keyboard, track ball, touch activated screen, light wand, voice control, or any similar or equivalent input device, and may be used for interactive geometry prescription.

The system control computer 32 includes a set of modules in communication with each other via electrical and/or data connection 32a. Data connections 32a may be direct wired links, or may be fiber optic connections or wireless communication links or the like. In alternative embodiments, the modules of computer system 20 and system control computer 32 may be implemented on the same computer system or a plurality of computer systems. The modules of system control computer 32 include a CPU module 36 and a pulse generator module 38 that connects to the operator console 12 through a communication link 40. The pulse generator module 38 may alternatively be integrated into the scanner equipment (e.g., resonance assembly 52). It is through link 40 that the system control computer 32 receives commands from the operator to indicate the scan sequence that is to be performed. The pulse generator module 38 operated the system components that play out (i.e., perform) the desired pulse sequence by sending instructions, commands and/or requests describing the timing, strength and shape of the RF pulses and pulse sequences to be produced and the timing and length of the data acquisition window. The pulse generator module 38 connects to a gradient amplifier system 42 and produces data called gradient waveforms that control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of Gx, Gy and Gz amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of a resonance assembly 52 that includes a polarizing superconducting magnet with superconducting main coils 54. Resonance assembly 52 may include a whole-body RF coil 56, surface or parallel imaging coils 76 or both. The coils 56, 76 of the RF coil assembly may be configured for both transmitting and receiving or for transmit-only or receive-only. A patient or imaging subject 70 may be positioned within a cylindrical patient imaging volume 72 of the resonance assembly 52. A transceiver module 58 in the system control computer 32 produces pulses that are amplified by an RF amplifier 60 and coupled to the RF coils 56, 76 by a transmit/receive switch 62. The resulting signals emitted by the excited nuclei in the patient may be sensed by the same RF coil 56 and coupled through the transmit/receive switch 62 to a preamplifier 64. Alternatively, the signals emitted by the excited nuclei may be sensed by separate receive coils such as parallel or surface coils 76. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the RF coil 56 during the receive mode. The transmit/receive switch 62 can also enable a separate RF coil (for example, a parallel or surface coil 76) to be used in either the transmit or receive mode.

The MR signals sensed by the RF coil 56 or parallel or surface coil 76 are digitized by the transceiver module 58 and transferred to a memory module 66 in the system control computer 32. Typically, frames of data corresponding to MR signals are stored temporarily in the memory module 66 until they are subsequently transformed to create images. An array processor 68 uses a known transformation method, most commonly a Fourier transform, to create images from the MR signals. These images are communicated through the link 34 to the computer system 20 where it is stored in memory. In response to commands receive from the operator console 12 this image data may be archived in long term storage or it may be further processed by the image processor 22 and conveyed to the operator console 12 and presented on display 16.

Figure 2:
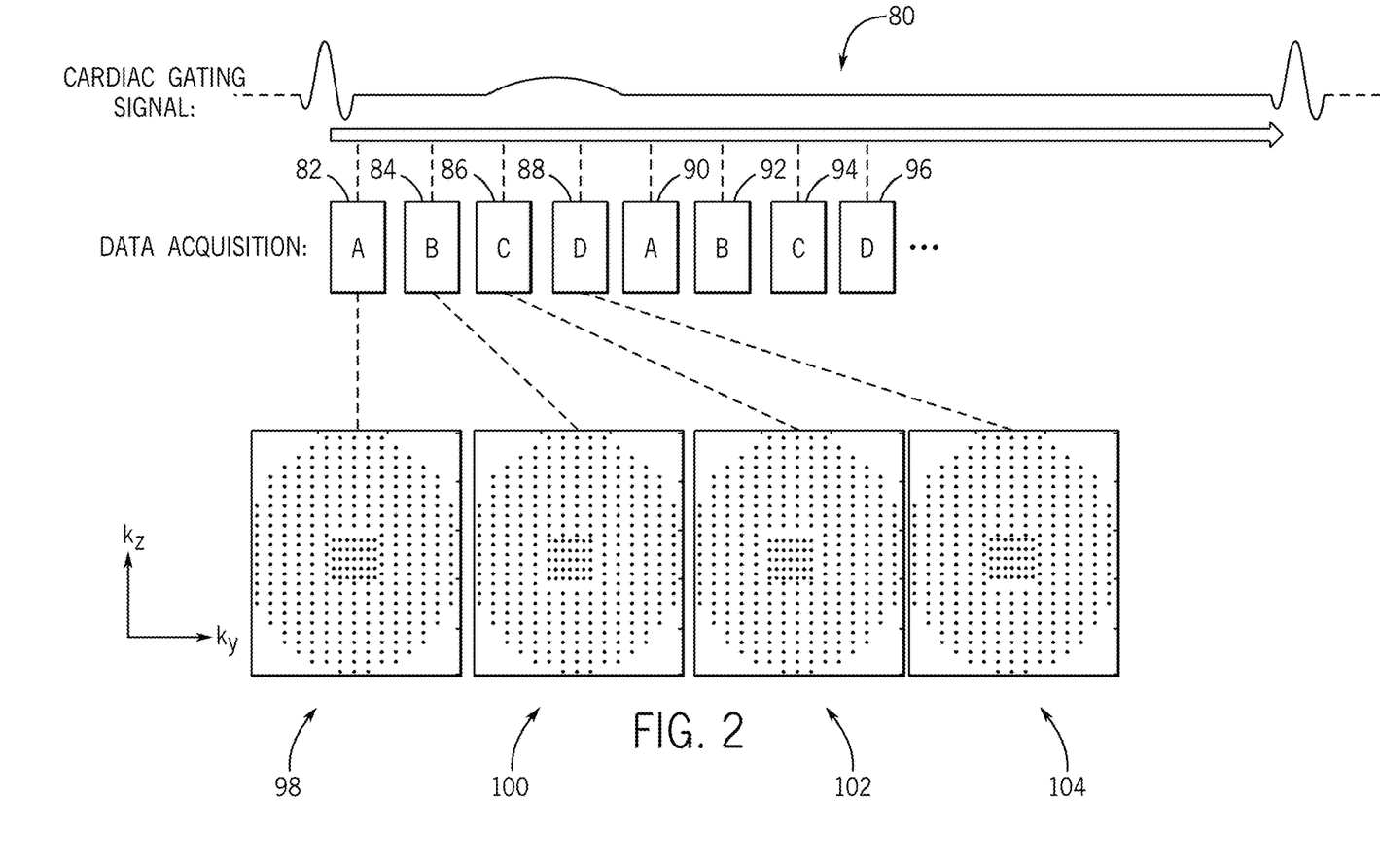
FIG. 2 is a schematic diagram of MRI k-space data acquisition.

Referring to FIG. 2 MRI data is acquired from a patient over a period of time where there is a cognizable variation in the signals from dynamic tissue. In one embodiment the dynamic event is the beating heart as illustrated as cardiac signal 80. In one embodiment the scan or MRI examination is conducted over the course of one breath hold for the human patient being examined. MRI data is acquired over a period of time in which the dynamic event is occurring. In one embodiment, MRI data is acquired at different time intervals. In one embodiment time shifted MRI k-space data, indicated by 82, 84, 86, 88, 90, 92, 94, and 96, are acquired and such data may be utilized to analyze which voxels represent tissue that is substantially static and which voxels represent tissue that is substantially dynamic such as certain portion of the heart which move over the period of time in which the MRI data is collected. In one embodiment a sliding window method as known in the art may be used to reconstruct a plurality of time frame images during the cardiac cycle. The number of time frames may be between 2 and 4 or greater than 4. K-spaced data 82-88 are illustrated as reference 98-104 in FIG. 2.

The selection of time windows requires some minimal knowledge of the dynamic event such that each time window captures the dynamic tissue in a different place in its movement path or with different signal intensity. For instance, if the dynamic event is a beating heart the subset of pre-processed time windows should be different portions of the cardiac cycle. Images can then be reconstructed from the signals from each time window as described in more detail below.

Figure 3:
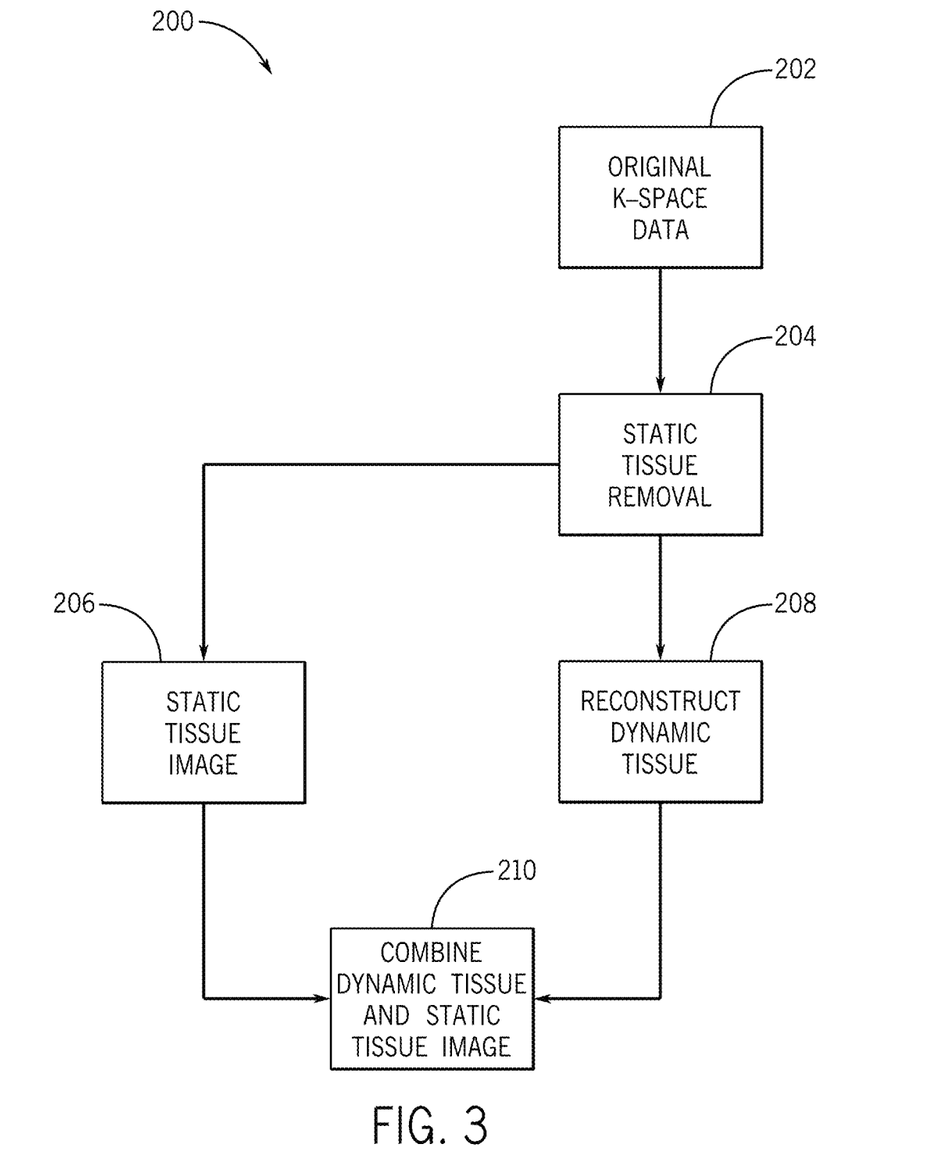
FIG. 3 is a process flow diagram of an embodiment of a method for processing MRI data.
Figure 4:
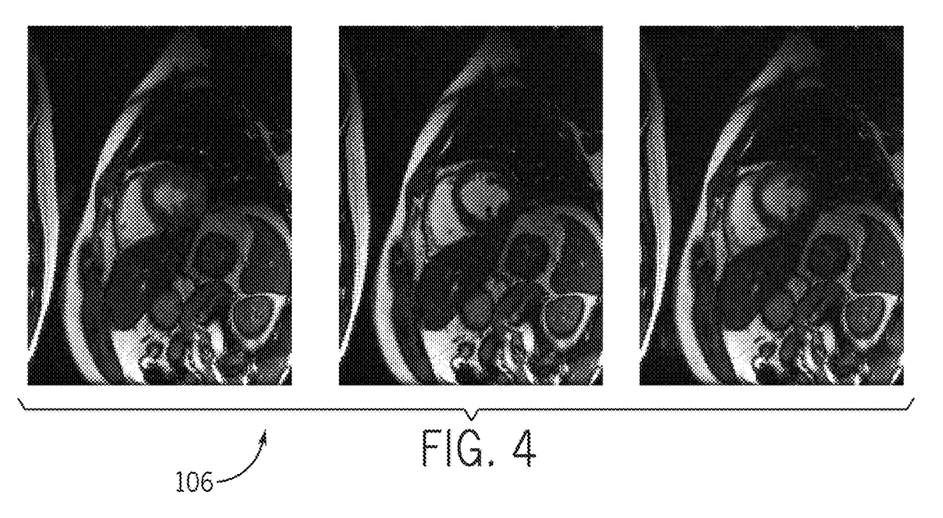
FIG. 4 is a series of MRI images, each created from the signal data from one of three different time windows in a cardiac cycle which are triggered at the start of, one third and two thirds into the cardiac cycle.

Referring to FIGS. 3-6, a process 200 of processing MRI data will be described. In a step 202 original k-space data from an MRI scan is obtained and stored. The original k-space data is acquired as discussed above over a period of time in which a dynamic event such as the beating of a heart occurs. In a step 204, the voxels representing the static tissue of the MRI scan is determined. Referring to FIG. 2 selected frames of the MRI data that are time shifted over the course of the dynamic event are reconstructed. In one embodiment the k-space MRI data that is reconstructed maybe a frame combined from data A-D in a temporal neighborhood on FIG. 2. Referring to FIG. 4 three frames may be created so they display the start of and one third and two thirds into a cardiac cycle of a beating human heart. Referring to FIG. 4 three time spaced frames are reconstructed illustrating the heart and surrounding tissue at three different phases of the heartbeat. In other embodiments the number of frames selected for reconstruction from the original MRI data may be as few as two, or more than three such as four or more.

The signal dynamics of the voxels in each of the reconstructed images from the time spaced frames are compared to one another. The signal dynamics may be the value associated with the signal intensity of each voxel in the reconstructed images. The greater the difference in the signal dynamics between the voxels in the reconstructed images the greater the likelihood that the voxels represent dynamic tissue. The small the difference in the signal dynamics between the reconstructed images the greater the likelihood that the voxels represent static tissue.

Figure 7:
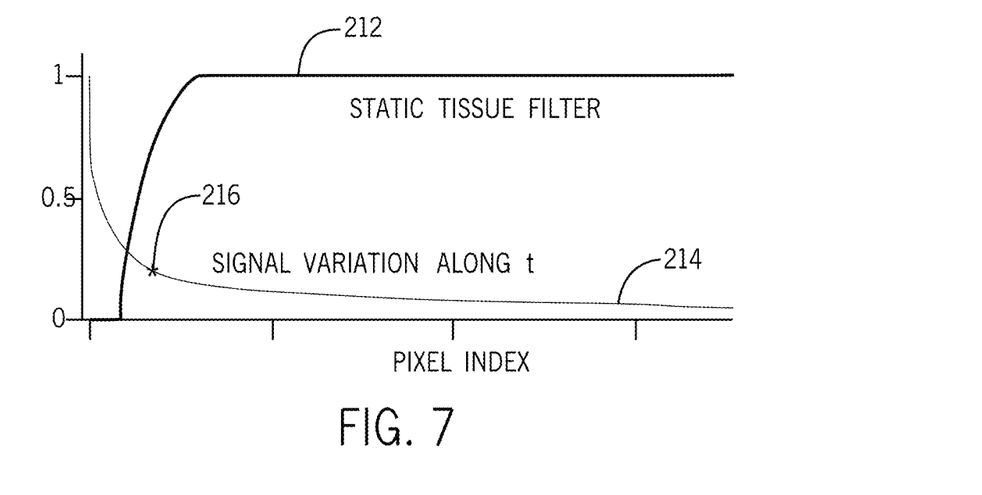
FIG. 7 is a plot used to set a threshold point.

Referring to FIG. 7 in one embodiment an analysis can be performed to quantify the amount of variation of each voxels or pixels between the time spaced images. A normalized number assigned to each voxel or pixel indicative of how much it (or more precisely its signal dynamics) changes with time. The highest difference in signal dynamics between voxels in the time spaced images is accorded a value of first value such as 1. If there is no difference then the voxel is accorded a value of 0. The voxels are then accorded a value between 0 and 1 depending on the relationship between the highest difference and no difference.

A plot 214 can be constructed of this normalized signal variation versus the voxel or pixel identity with the identity resorted on the x-axis to place the voxels or pixels with the highest image signal variation at the origin. From this plot a point 216 at which the image signal strength begins to sharply increase can be identified and used as a threshold value. There are many ways in which point 216 may be identified. In one embodiment the maximum rate of curvature may be used to set threshold point 216.

A normalized plot 212 can then be constructed by assigning a relative weight to each voxel with those representing static tissue being assigned a value of one at one extreme and those voxels representing dynamic tissue being assigned a value of zero at the other extreme.

Figure 5:
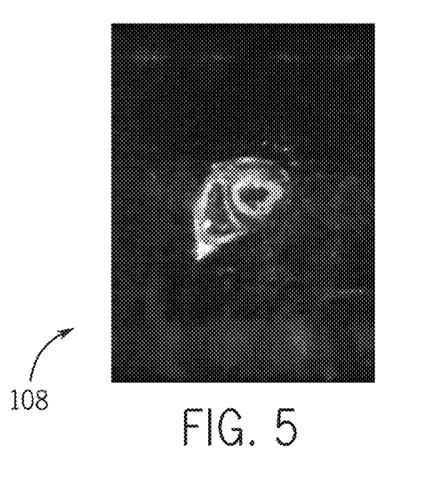
FIG. 5 is an MRI image created from the signal data after the voxels have been assigned a value of based on the pixel index differences between time shifted reconstructed images.

Referring to FIG. 5, after each voxel is assigned a value of zero or one as discussed above, an image may be created. In this image the voxels representing dynamic tissue have a high light intensity while the voxels that represent static tissue have a low light or no light intensity.

Figure 6:
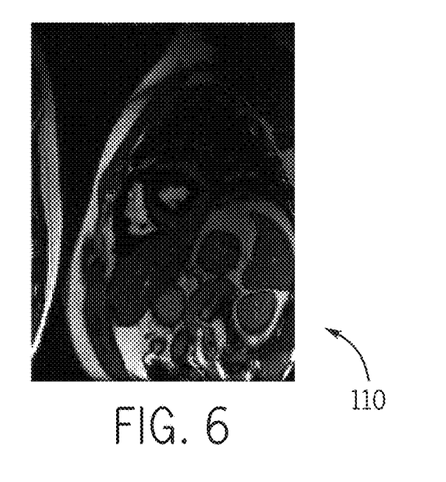
FIG. 6 is a static MRI image created from the signal data including only the signal data which remained essentially constant over the time windows of FIG. 1.

In a step 206, a static tissue image is created including only the voxels that were identified as representing static tissue. The static tissue image may be created from a single time frame of the original MRI data, or the static tissue image may be created by averaging all the original MRI data. The averaging of all the acquired data identified as representing static tissue minimizes the noise that may be present in the MRI data. Referring to FIG. 6 a static tissue image may then be stored for later use as described below.

In one embodiment a static image can be constructed from the voxels or pixels that have been assigned a weight greater than zero using their relative weights. This image of the static tissue in the Field of View (FOV) can now be converted into k-space and subtracted from the k-space data acquired in imaging the dynamic event. The so-generated modified k-space data after the subtraction contains signal from dynamic tissue and will be processed as described below.

In a step 208, only the voxels representing dynamic tissue are reconstructed from the modified k-space MRI data. This significantly improves the conditioning of unaliasing reconstruction and reduces the processing time required to reconstruct the MRI data. As a result the dynamic voxels can be reconstructed with higher accuracy and with at much quicker speed than if the static voxels for each frame had to be reconstructed as well.

In a step 210 the reconstructed dynamic voxels are combined with the single static tissue image, such that each frame of the final MRI images used for diagnostics include the reconstructed dynamic voxels from each frame combined with the single static tissue image created in step 206.

In one embodiment, the signal energy after the subtraction is used to identify those locations which do not encompass voxels associated with the dynamic event and such locations are excluded from the subsequent unaliasing reconstruction of an image from the voxels associated with the dynamic event. After the signals representing static tissue have been estimated and subtracted, it may be reasonably assumed that only voxels contributing significant signal strength contain dynamic tissue. Therefore those locations which have low signal may be eliminated from further data processing. In one embodiment, such locations with low signal correspond to readout slices not covering any dynamic tissue voxel.

Figure 8:
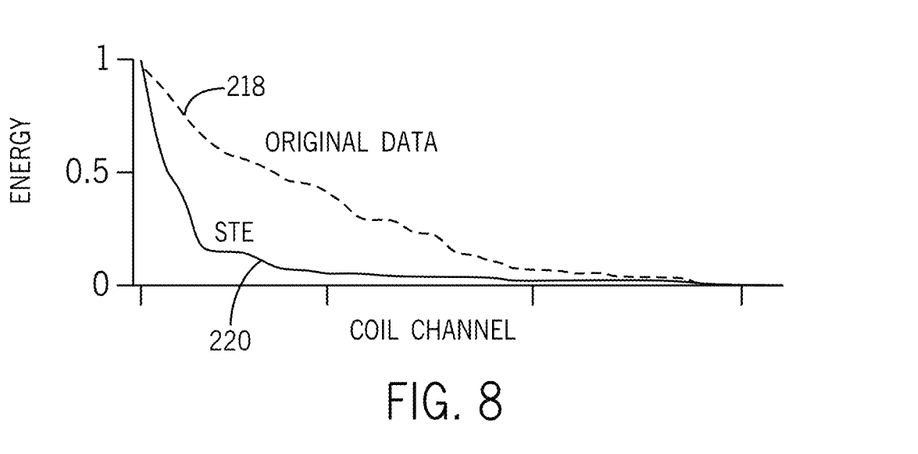
FIG. 8 is a plot of signal energy versus coil channel.

Referring to FIG. 8, in one embodiment the coil channels which are not reporting signals associated with the dynamic event may be identified and have their signals eliminated from further data analysis once the static tissue signals have been subtracted. A plot of signal energy versus coil channel may be constructed for both the full scan (dashed line) and the scan after subtraction of the signal representative of the static tissue (solid line). Once the static tissue signal has been subtracted it becomes relatively easy to identify those coil channels which are not sensing any signal from the dynamic event. It facilitates further data processing to eliminate the signal provided by these coil channels. In particular, the data from these channels may be eliminated in the subsequent unaliasing reconstruction of an image from the voxels associated with the dynamic event.

In one embodiment, a static image is constructed from the voxels for which there is a significant signal which has substantially no change between the sampled time windows, the image is converted into k-space and subtracted from the k-space representation of the entire scan and the residual k-space data is subject to unaliasing reconstruction. In the data acquisition step of accelerated MRI less data is collected than in the case of unaccelerated MRI examination. This is commonly described as under sampling k-space. There are a number of mathematical techniques for reconstructing the k-space representation to accommodate the under sampling while minimizing the creation of image artifacts when the k-space data is transformed to image data by an inverse Fournier transform. These techniques can be generally described as unaliasing reconstruction and include such techniques as k-t auto-calibrating parallel imaging (acPI). The efficiency of these unaliasing reconstruction techniques both in terms of final image quality and computation time is significantly improved if the k-space data set is reduced by the subtraction of the k-space data representative of the static image.

In one embodiment, the image obtained from the unaliasing reconstruction of the residual k-space data and the static image are combined to yield a final image. Because the static tissue image is a full coil-element and full x-location image, the final reconstruction is a full FOV image with no signal loss compared to conventional reconstruction.

In one embodiment an MRI method can remove static tissue signal estimated from k-t accelerated data acquisition before k-t or parallel imaging reconstruction for improving image quality and meanwhile can detect and eliminate non-dynamic-tissue coil elements and locations from reconstruction processing for much faster computation.

In one embodiment, a k-t accelerated imaging performs time-shifted k-space acquisition. In one step it is possible to reconstruct a few scouting frames using view-sharing, for example, 3 frames with temporal delay of 0, ⅓ and ⅔ scan time. In another step calculation of voxel-wise signal variations along time on the scouting images to differentiate static tissues (voxels with low temporal variation) and dynamic tissues (voxels with high temporal variation). A static-dynamic tissue threshold can be auto-selected on the temporal dynamics curve and used to obtain a static tissue image containing voxels with below-threshold temporal dynamics. The static tissue image may be converted back to k-space and subtracted from acquired k-space data. The subsequent k-t construction is performed on residual signal to resolve aliasing on dynamic tissues only. Because removing static tissue largely sparsifies the image content and thereby substantially reduces the severity of aliasing in acquired data, the conditioning of k-t reconstruction is much improved compared to conventional k-t reconstruction on the original k-space data and provides higher image quality (less residual aliasing artifacts and higher signal to noise ratio).

Referring to FIG. 8, after removing static tissue signals, the image content contains signals from dynamic tissue only (the heart in cardiac imaging). With high density coils, many peripheral coil elements far away from the heart contribute mostly noise. By comparing the signal energy of different coil elements, it is possible to auto-detect noise-only coil elements and eliminate them from reconstruction data processing. Also, for an ARC-type reconstruction, is possible to convert the original k-space data into hybrid x-k space by Fourier transform along readout and then perform reconstruction x-location-by-x-location on the hybrid space data. Such reconstruction is effective only on x-locations containing dynamic tissues near the heart and is essentially fitting noise on peripheral x-locations. Therefore, by analyzing the signal energy along readout on the hybrid space data, it is possible to auto-detect and eliminate noise-only x-locations for faster computation. This method enables E-coil square times faster computation in both calibration and synthesis plus additionally E-x times faster computation in synthesis, where E-coil and E-x indicate the factor of peripheral coil and x-location elimination, respectively.

In one embodiment after recovering dynamic tissue using k-t reconstruction, it is possible to add the static tissue signal back to the reconstructed data as the final reconstruction. Because the static tissue image is a full coil-element and full x-location image, the final reconstruction is a full FOV image with no signal loss.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A method for accelerated magnetic resonance imaging (MRI) scan, the method comprising:
   acquiring original under-sampled k-space data from an MRI scan on a subject over a period of time;
   reconstructing multiple time spaced scout frames from the original under-sampled k-space data;
   identifying static tissue voxels that represent static tissue of the subject in the multiple time spaced scout frames;
   generating a static tissue image from the static tissue voxels;
   converting the static tissue image to k-space to generate static k-space data;
   removing the static k-space data from the original under-sampled k-space data to generate under-sampled dynamic k-space data;
   reconstructing a dynamic tissue image from the under-sampled dynamic k-space data;
   combining the static tissue image and the dynamic tissue image to generate a final image;
   wherein identifying the static tissue voxels comprises:
   comparing signal variation of each voxel between the multiple time spaced scout frames with a threshold value;
   determining a particular voxel to be static tissue voxel in response to the signal variation of the particular voxel being less than the threshold value, wherein the signal variation is a normalized signal variation; and
   wherein the threshold is a maximum rate of curvature of a plot between the normalized signal variation and voxel identity.

2. The method of claim 1, wherein reconstructing the dynamic tissue image from the under-sampled dynamic k-space data comprises using a data completion reconstruction method synthesizing unsampled data in k-space or a transformed data domain.

3. The method of claim 2, wherein the data completion reconstruction method comprises k-t auto-calibrating parallel imaging (acPI).

4. The method of claim 1, further comprising:
   identifying a set of coil channels which contribute only noise to the dynamic k-space data; and
   eliminating signals from the coil channels from reconstructing the dynamic tissue image.

5. The method of claim 1, wherein the MRI scan is performed on a heart of the subject.

6. A magnetic resonance imaging (MRI) system, the system comprising:
   coil channels configured to acquire original under-sampled k-space data from an MRI scan on a subject over a period of time; and
   a processor configured to:
   reconstruct multiple time spaced scout frames from the original under-sampled k-space data;
   identify static tissue voxels that represent static tissue of the subject in the multiple time spaced scout frames;
   generate a static tissue image from the static tissue voxels;
   convert the static tissue image to k-space to generate static k-space data;
   remove the static k-space data from the original under-sampled k-space data to generate under-sampled dynamic k-space data;

reconstruct a dynamic tissue image from the undersampled dynamic k-space data;
combine the static tissue image and the dynamic tissue image to generate a final image;
wherein the processor is further configured to identify the static tissue voxels by:
  comparing signal variation of each voxel between the multiple time spaced scout frames with a threshold value;
  determining a particular voxel to be static tissue voxel in response to the signal variation of the particular voxel being less than the threshold value, wherein the signal variation is a normalized signal variation; and
  wherein the threshold is a maximum rate of curvature of a plot between the normalized signal variation and voxel identity.

7. The MRI system of claim 6, wherein the multiple time spaced scout frames are evenly temporally spaced.

8. The MRI system of claim 6, wherein reconstructing the dynamic tissue image from the dynamic k-space data comprises using a data completion reconstruction method synthesizing unsampled data in k-space or a transformed data domain.

9. The MRI system of claim 8, wherein the data completion reconstruction method comprises k-t auto-calibrating parallel imaging (acPI).

10. The MRI system of claim 6, wherein the processor is further configured to:
  identify a set of coil channels which contribute only noise to the dynamic k-space data; and
  eliminate signals from the coil channels from reconstructing the dynamic tissue image.

11. The MRI system of claim 6, wherein the MRI scan is a cardiac MRI scan.

12. The method of 1, wherein the multiple time spaced scout frames are evenly temporally spaced.

* * * * *